(12) United States Patent
Kallupalayam Ramasamy et al.

(10) Patent No.: US 11,492,303 B2
(45) Date of Patent: Nov. 8, 2022

(54) PROCESSES FOR THE CONVERSION OF MIXED OXYGENATES FEEDSTOCKS TO HYDROCARBON FUELS

(71) Applicant: BATTELLE MEMORIAL INSTITUTE, Richland, WA (US)

(72) Inventors: Karthikeyan Kallupalayam Ramasamy, West Richland, WA (US); Mond F. Guo, Richland, WA (US); Senthil Subramaniam, Richland, WA (US); Udishnu Sanyal, Richland, WA (US); Casper O. Brady, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 17/318,204

(22) Filed: May 12, 2021

(65) Prior Publication Data
US 2021/0269377 A1 Sep. 2, 2021

Related U.S. Application Data

(63) Continuation-in-part of application No. 16/265,553, filed on Feb. 1, 2019, which is a continuation-in-part of application No. 15/871,773, filed on Jan. 15, 2018, now Pat. No. 10,221,119.

(60) Provisional application No. 63/024,362, filed on May 13, 2020, provisional application No. 62/452,143, filed on Jan. 30, 2017.

(51) Int. Cl.
| | | |
|---|---|---|
| C07C 45/45 | (2006.01) | |
| C07C 1/00 | (2006.01) | |
| C07B 31/00 | (2006.01) | |
| C10G 3/00 | (2006.01) | |
| C07C 1/22 | (2006.01) | |
| C10L 1/04 | (2006.01) | |

(52) U.S. Cl.
CPC .............. C07C 1/22 (2013.01); C07B 31/00 (2013.01); C10G 3/44 (2013.01); C10G 3/50 (2013.01); C10L 1/04 (2013.01); C10G 2400/08 (2013.01); C10L 2200/04 (2013.01); C10L 2290/10 (2013.01)

(58) Field of Classification Search
CPC ............ C07C 45/45; B01J 23/72; B01J 23/80
See application file for complete search history.

(56) References Cited

PUBLICATIONS

Onyestyak et al. Upgraded biofuel from alcohol-acetone feedstocks over a two-stage flow-though catalytic system. Catalysis Science & Technology vol. 6, 4516-4524. (Year: 2016).*
Gurbuz et al. Dual-bed catalyst system for C-C coupling of biomass-derived oxygenated hydrocarbons to fuel-grade compounds. Green Chemistry, vol. 12, 223-227. (Year: 2010).*

* cited by examiner

*Primary Examiner* — Sikarl A Witherspoon
(74) *Attorney, Agent, or Firm* — Derek H. Maughan

(57) ABSTRACT

A method for forming a desired hydrocarbon fuel product from a mixed oxygenate feedstock by utilizing chemical processes to form ketones from the oxygenate feed, upgrade the ketones, recycle selected upgraded ketones through the upgrading process to obtain a desired intermediate and hydrogenating the desired intermediate to obtain the desired hydrocarbon fuel product. In various alternative configurations and embodiments this can be accomplished in a number of ways, and originate in a number of different positions and occasions.

14 Claims, 16 Drawing Sheets

FIG. 3A

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature | Zr:Zn(2:1) | Pd(0.05) | 340 | 93.59% | 11.46% | 20.64% | 10.63% | 2.75% | 1.04% | 0.21% | 8.04% | 10.72% | 7.78% | 24.20% | 2.52% |
| | Zr:Zn(2:1) | Pd(0.05) | 355 | 98.81% | 13.93% | 29.05% | 16.62% | 5.86% | 1.66% | 0.50% | 12.32% | 7.79% | 5.05% | 3.51% | 3.71% |
| | Zr:Zn(2:1) | Pd(0.05) | 370 | 99.51% | 10.92% | 29.04% | 18.42% | 6.94% | 3.64% | 0.70% | 14.10% | 3.07% | 1.21% | 0.43% | 11.53% |

FIG. 3B

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature +Potassium | Zr:Zn(2:1) | Pd(0.05)+1%K | 340 | 95.89% | 13.08% | 27.53% | 12.95% | 3.01% | 0.93% | 0.20% | 9.91% | 9.94% | 6.57% | 13.10% | 2.76% |
| | Zr:Zn(2:1) | Pd(0.05)+1%K | 355 | 99.42% | 13.06% | 31.60% | 18.61% | 5.59% | 1.42% | 0.38% | 10.93% | 7.09% | 4.53% | 1.16% | 5.62% |
| | Zr:Zn(2:1) | Pd(0.05)+1%K | 370 | 99.02% | 12.49% | 29.68% | 17.32% | 6.23% | 3.04% | 0.59% | 14.20% | 3.99% | 1.88% | 0.79% | 9.79% |

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature | Zr/Zn(2:1) | Pd(0.1) | 340 | 95.66% | 10.39% | 24.02% | 13.73% | 3.91% | 1.27% | 0.33% | 9.29% | 7.36% | 10.55% | 16.38% | 2.78% |
| | Zr/Zn(2:1) | Pd(0.1) | 355 | 98.99% | 10.44% | 28.88% | 19.79% | 7.73% | 2.05% | 0.62% | 12.39% | 6.25% | 4.86% | 1.70% | 5.32% |
| | Zr/Zn(2:1) | Pd(0.1) | 370 | 99.52% | 7.64% | 25.13% | 21.61% | 7.49% | 5.13% | 1.05% | 13.83% | 2.62% | 0.87% | 0.35% | 14.08% |

FIG. 3C

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature +Potassium | Zr/Zn(2:1) | Pd(0.1)+1%K | 340 | 95.45% | 9.18% | 26.95% | 15.58% | 3.98% | 1.02% | 0.30% | 10.08% | 7.55% | 8.76% | 13.61% | 3.08% |
| | Zr/Zn(2:1) | Pd(0.1)+1%K | 355 | 98.79% | 11.26% | 31.34% | 18.95% | 5.92% | 1.47% | 0.36% | 13.20% | 6.21% | 3.85% | 1.48% | 5.96% |
| | Zr/Zn(2:1) | Pd(0.1)+1%K | 370 | 99.54% | 10.37% | 28.51% | 20.44% | 6.54% | 3.55% | 0.54% | 13.92% | 2.84% | 0.71% | 1.06% | 11.52% |

| Notes | Mixed Oxide (ratio) | Metal (wt%) | Temperature (°C) | Ethanol Conversion (%) | Selectivity % |||||||||||
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| ZrZn with 1 to 2 ratio at different temperature | ZrZn(1:2) | Pd(0.1) | 340 | 91.66 | 7.22% | 18.27% | 8.88% | 3.37% | 0.78% | 0.26% | 7.20% | 8.13% | 11.44% | 31.61% | 2.85% |
| | ZrZn(1:2) | Pd(0.1) | 355 | 97.2 | 9.21% | 26.45% | 15.91% | 6.22% | 1.73% | 0.53% | 11.15% | 7.43% | 9.42% | 8.99% | 2.95% |
| | ZrZn(1:2) | Pd(0.1) | 370 | 99.78 | 8.63% | 29.86% | 19.24% | 8.94% | 5.18% | 0.80% | 11.88% | 3.60% | 4.67% | 0.65% | 6.55% |

FIG. 3F

| Notes | Mixed Oxide (ratio) | Metal (wt%) | Temperature (°C) | Ethanol Conversion (%) | Selectivity % |||||||||||
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| ZrZn with 1 to 1 ratio at different temperature | ZrZn(1:1) | Pd(0.1) | 340 | 84.27 | 5.21% | 11.16% | 6.58% | 1.65% | 0.67% | 0.05% | 4.47% | 7.45% | 12.36% | 47.81% | 2.55% |
| | ZrZn(1:1) | Pd(0.1) | 355 | 91.95 | 8.17% | 19.80% | 11.29% | 3.04% | 1.18% | 0.16% | 8.89% | 7.83% | 10.03% | 25.96% | 3.72% |
| | ZrZn(1:1) | Pd(0.1) | 370 | 97.7 | 11.04% | 26.49% | 13.42% | 6.41% | 2.83% | 0.61% | 13.56% | 5.63% | 5.65% | 8.41% | 5.95% |

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| | ZrZn(2:1) | | 370 | 60.46 | 6.02% | 2.18% | 1.21% | 0.16% | 0.00% | 0.00% | 5.63% | 2.83% | 8.13% | 34.15% | 39.09% |
| | ZrZn(2:1) | Cu(1) | 370 | 95.08 | 12.95% | 24.55% | 12.69% | 4.57% | 0.86% | 0.19% | 11.79% | 7.31% | 7.93% | 8.93% | 8.32% |
| | ZrZn(2:1) | Ag(0.5) | 370 | 99.71 | 16.33% | 22.97% | 7.75% | 2.23% | 0.63% | 0.80% | 19.25% | 2.34% | 0.56% | 0.17% | 26.98% |
| | ZrZn(2:1) | Pt(0.1) | 370 | 99.3 | 8.72% | 24.74% | 12.20% | 4.78% | 1.41% | 0.44% | 12.19% | 3.39% | 2.65% | 2.59% | 26.90% |
| Different metal impregnations | ZrZn(2:1) | Pd(0.05) | 370 | 99.91 | 9.53% | 27.65% | 16.09% | 7.39% | 5.14% | 2.28% | 14.25% | 3.19% | 1.88% | 1.88% | 10.73% |
| | Zr | Pd(0.1) | 370 | 55.47 | 1.86% | 5.82% | 1.02% | 0.07% | 0.00% | 0.00% | 3.28% | 17.84% | 1.08% | 2.24% | 66.80% |

FIG. 3G

PROCESSES FOR THE CONVERSION OF MIXED OXYGENATES FEEDSTOCKS TO HYDROCARBON FUELS

PRIORITY

This application claims priority from U.S. Patent Application No. 63/024,632 filed by the same inventors on May 13, 2020. The contents of which are hereby incorporated by reference in their entirety.

FEDERALLY-SPONSORED RESEARCH AND DEVELOPMENT

This invention was made with Government support under Contract DE-AC0576RL01830 awarded by the U.S. Department of Energy. The Government has certain rights in the invention.

BACKGROUND OF THE INVENTION

Field of the Invention

The invention generally relates to chemical and chemical synthesis and more particularly to systems and methodologies for upgrading and modifying alcohols such as ethanol and other oxygenates such as acetaldehyde and ethyl acetate to higher products such as ketones with carbon number $>C_3$. These ketones are further converted to (jet) fuel range hydrocarbons.

Background Information

Alcohols, particularly ethanol, are widely available commercially produced chemicals with domestic production greater than 15 billion gallons. Despite their availability, broader utilization of alcohol-based products in fuels has been limited due to a variety of factors. Among these factors is the so called "blend wall", whereby the inclusion of alcohols in various applications is limited because of concerns about negative associated complications. For example, in gasoline markets ethanol mixing is deemed by some to be a negative (e.g., lower energy density). Other types of higher order fuels do not have these same problems and are included into fuel mixtures without blend limitations. In addition, efficiently upgraded feedstocks such as ethanol that form higher value products can be utilized as replacements (in whole or in part) from fossil derived materials. Hence, a need exists to cheaply and efficiently upgrade ethanol to form chemical feedstocks. The present application contains developments that meet these needs.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY

The present application describes a method for forming a desired hydrocarbon fuel product from a mixed oxygenate feedstock by utilizing chemical processes to form ketones from the oxygenate feed, upgrade the ketones, recycle selected upgraded ketones through the upgrading process to obtain a desired intermediate and hydrogenating the desired intermediate to obtain the desired hydrocarbon fuel product.

In various alternative configurations and embodiments this can be accomplished in a number of ways, and originate in a number of different positions and occasions.

In one arrangement the mixed oxygenate feedstock includes alcohols, aldehydes, esters, and carboxylic acids which can be converted to C2n−1 ketones. The ketone forming step may include passing the feedstock over a catalyst such as 0.1% Pd—ZnO—ZrO2 or 0.5% Pd—ZnO. The ketone upgrading step may also include passing the feedstock over a catalyst such as 0.1% Pd—ZnO—ZrO2 and 0.5% Pd—ZnO. The average ketone carbon chain length can be varied from ~4 to ~6 by lowering the weight hourly space velocity from 0.69 to 0.15 hr-1 or increasing the reaction temperature from 340° C. to 370° C. In some instances, the hydrogen gas utilized to perform hydrogenation is generated in-situ through the formation of acetone. In some circumstances the upgrading step may include dimerization over a catalyst selected from the group consisting of MgO—$Al_2O_3$ and 0.01% to 1% Pd—MgO—$Al_2O_3$ and or be performed by a condensation chemistry reaction.

In some circumstances the upgrading steps may include aromatization using an acid catalyst, trimerization of smaller ketones over a catalyst such as MgO—Al2O3 and 0.01% to 1% Pd—MgO—Al2O3 or other similar processes. The desired intermediate may be a branched cyclohexenone product. The basic methodology can also be modified by including a step of performing a hydrodeoxygenation process to form alkanes, isoalkanes and cycloalkanes. This may include passing C9-15 cyclic and linear ketone mixtures over MgO—Al2O3, using a nickel-based hydrogenation catalyst. In other embodiments, other feedstocks, intermediates, and chemical processes aligned with the foregoing can be utilized and modified according to the needs and necessities of a user.

Various additional advantages and novel features of the present disclosure are described herein and will become further readily apparent to those skilled in this art from the following detailed description. As will be realized, the disclosure is capable of modification in various respects without departing from the disclosure. Accordingly, the drawings and description of the preferred embodiment set forth hereafter are to be regarded as illustrative in nature, and not as restrictive.

BRIEF DESCRIPTION OF THE DRAWINGS

FIG. 3A-3G show the results of various forms of ethanol cross aldol testing obtained on various examples.

DETAILED DESCRIPTION

As described in detail below in one embodiment a process is provided wherein conversion of ethanol to $C_{5+}$ ketones in one single catalytic step (mixed metal oxide) or to $C_{5+}$ alcohols in dual catalytic step (mixed metal oxide followed by mild hydrogenation catalyst) with overall carbon efficiency greater than 83% at mild operating conditions (temperature between 300-400° C. and a pressure of atmospheric-500 psig) was performed. The results of this particular embodiment demonstrated that at 370° C. and 300 psig, there is 80% selectivity to $C_5$ to $C_{11}$ ketones. 2-pentanone, 2-heptanone, 4-heptanone and 4-nonanone are the major products. These materials can then be distilled and sold as ketones to be used as value added chemicals. Operating at higher temperature (>370° C.) will result in producing ketones with higher carbon number (higher molecular weight compounds) and cyclic compounds (e.g., phenolics and aromatics).

This methodology to upgrade ethanol using advanced carbon to carbon (C—C) coupling chemistry to produce a broad range of fuels and chemicals with very high carbon efficiency makes possible a variety of new applications. It is envisioned that in downstream applications this technology can be integrated to existing ethanol plants as an add-on process where fuels and commodity chemicals are produced in tandem and can also be alternatively configured and embodied as well.

Figure 1:
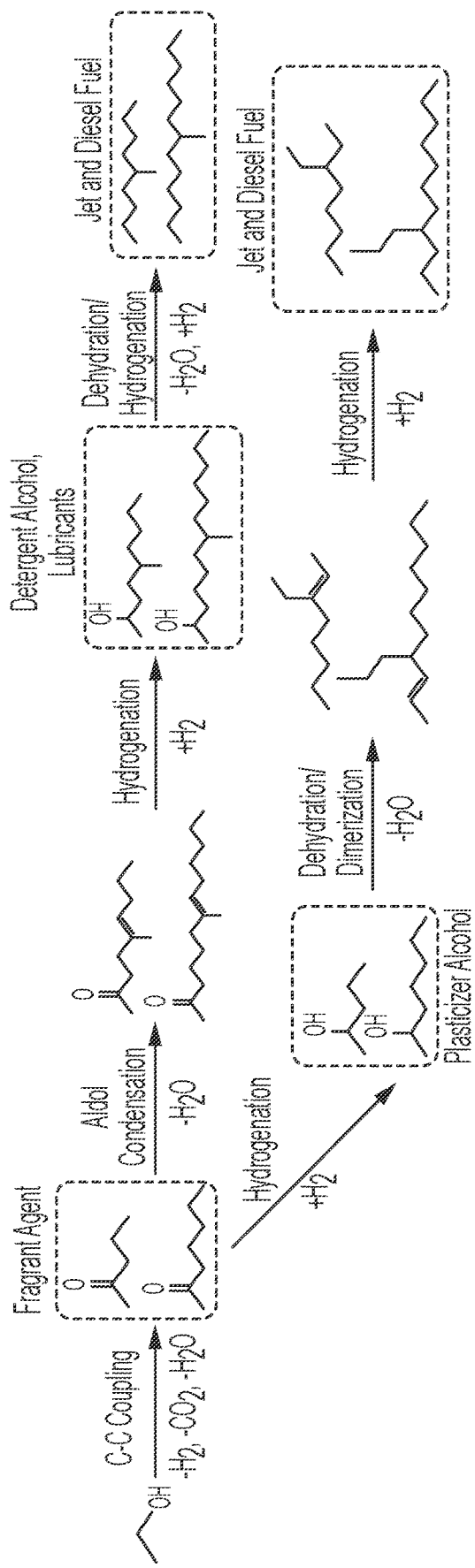
FIG. 1 shows examples of different chemistries involved in producing infrastructure compatible fuels and high value co-products through an ethanol to higher ketones pathway by utilizing known chemistries such as aldol condensation, dehydration and hydrogenation.

FIG. 1 depicts the different chemistries involved in producing infrastructure compatible fuels and high value co-products through an ethanol to higher ketones pathway by utilizing existing chemistries such as aldol condensation, dehydration and hydrogenation. As shown in FIG. 1, in one step ethanol is converted to $C_{5-11}$ ketones. The ketones mixture can be separated by simply distilling the ketones based on carbon numbers. These ketones can also be used as building blocks for other chemicals and fuels.

Further hydrogenation of these ketones generates alcohols in the oxo/plasticizer alcohols range. Through sequential dehydration, dimerization, and hydrogenation the plasticizer-range alcohol can be converted to jet fuel and diesel. Alternatively, self-aldol condensation of the $C_{5+}$ ketones followed by hydrogenation can produce detergent alcohols and lubricants. These higher alcohols can also be converted to jet fuel and diesel via a simple dehydration and hydrogenation. These are only a few of the potential routes that can be used to convert ethanol to valuable co-products and fuels via this demonstrated higher ketones pathway.

Due to the reactive nature and the higher carbon chain length ($C_{5-11}$) of the ketones generated from ethanol, this process provides significant potential opportunity and the versatility to produce various different valuable co-products of interest including fuels that can potentially help replace the whole barrel of crude oil. This higher ketones pathway would also enable a variety of newer opportunities that are otherwise not available via renewable means.

Figure 2:
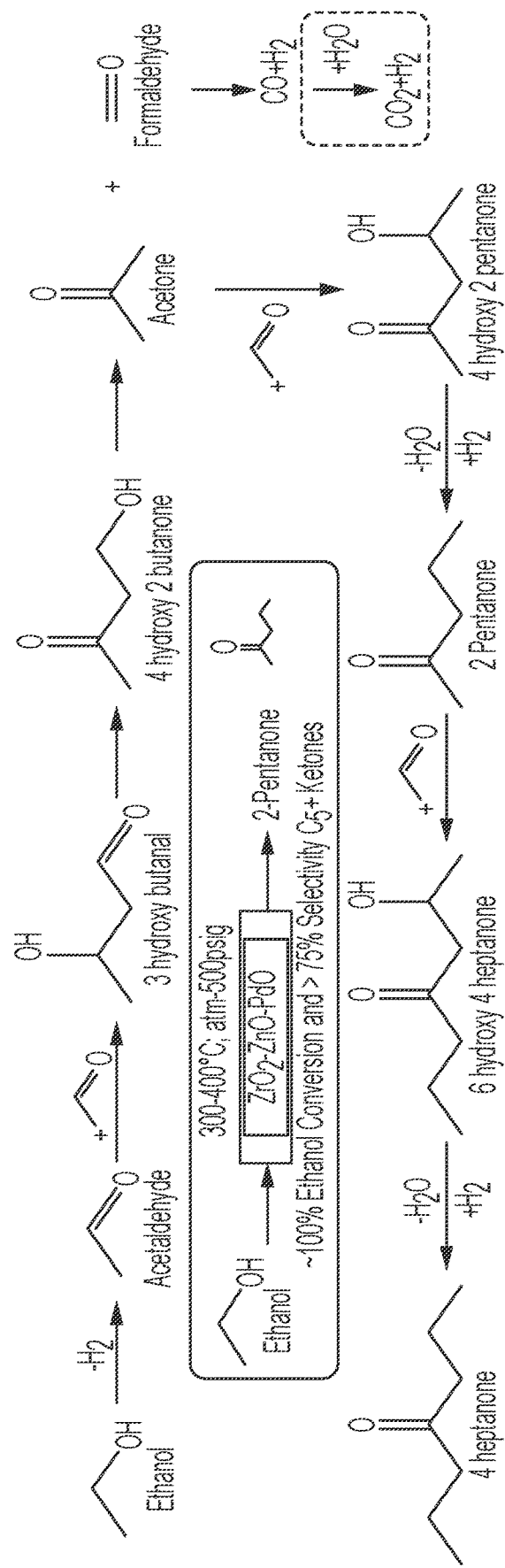
FIG. 2 shows the proposed chemistry, the process conditions and the major compounds generated from the ethanol to higher ketones process.

The present disclosure provides a description of recent work that has demonstrated a novel pathway to selectively convert ethanol and other mixed oxygenate feeds to hydrocarbon fuel through a $C_{5+}$ ketone-based pathway with minimal loss of carbon over a low cost multi-functional mixed oxide catalyst (ZrO2-ZnO) with >70% yield to $C_{5+}$ ketones. FIG. 2 shows the proposed chemistry, the process conditions and the major compounds generated from the ethanol to higher ketones process. In such an arrangement, a feedstock containing ethanol is passed over a mixed oxide catalyst having a promoter at temperatures between 300° C. and 400° C., pressure between atmospheric and 500 psig, and at a weight hourly space velocity between 0.1 hr$^{-1}$ and 1 hr$^{-1}$. Under these conditions the ethanol dehydrogenates to form acetaldehyde, which self-condense to form hydroxybutanal and then isomerizes (intermolecular hydride shift) to form hydroxybutanone, followed by retro-aldol reaction to form acetone and formaldehyde. Once acetone is formed it continuously reacts with acetaldehyde via cross aldol condensation to generate $C_{5+}$ ketones such as 2-pentanone and 2-heptanone (examples of higher ketone $C_{5+}$ products). The only step where carbon loss occurs is via the decomposition of formaldehyde during acetone formation.

The uniqueness of this chemistry lies in the condensation of acetone with acetaldehyde to form 2-pentanone rather than the self-condensation between acetone to form diacetone alcohol and mesityl oxide. These results are due to the unique combination of metal promoted mixed oxide catalyst providing the required acid, base and hydrogenation/dehydrogenation sites and help to improve the final product yield and reduce the overall carbon loss. Since the product chain growth occurs via the addition of acetaldehyde to higher ketones rather than acetone (cross aldol condensation), and the carbon loss occurs only in the acetone formation, leading to increased carbon efficiency with an increase in the carbon number of the ketones generated. For example, the theoretical carbon efficiency starting from ethanol for the formation of 2-pentanone and 4-nonanone is ~83% and ~90%, respectively. This also provides an opportunity to fine tune the chemistry to favor $C_{9+}$ ketones, further improving the carbon efficiency, product yield and potentially providing a pathway toward oxygenated value-added products.

The cascading nature of the chemistry in converting the alcohol to higher ketones requires a multi-functional catalytic system. The catalysts of interest are those exhibiting both acidic and basic properties. For example, mixed oxide materials such as ZrO2-ZnO, MgO—$Al_2O_3$, and MgO—$SiO_2$, along with promoter materials such as Ag, Pt, Pd, Cu, and Ni, are typically viewed as catalysts of interest. In general, bulk mixed-oxides are widely employed in industry as heterogeneous catalysts for selective oxidation, so the cost of the materials as well as the catalyst synthesis should be competitive.

In some applications alcohol conversion to generate $C_{5+}$ ketones over multi-functional catalyst(s) in a fixed bed reactor at 100% ethanol conversion and selectivity to ketones ≥80% can be completed under specified operating parameters such as temperature, pressure and space velocities. In other applications, $C_{5+}$ ketones hydrogenation to produce alcohols (e.g., plasticizer/oxo-alcohol) can be performed to achieve >90% conversion of the ketones with >90% selectivity to alcohols. Some other applications of the present invention include self-aldol condensation of the $C_{5+}$ ketone compounds followed by hydrogenation to form detergent and lubricant range alcohols. The conversion of renewable ethanol to fuels and chemicals can be performed in a biorefinery process by transforming ethanol to $C_{5-15}$ ketones→$C_{5-15}$ alcohols→jet and diesel fuel, with an overall carbon efficiency of 80% from ethanol to fuels and co-products.

The following examples provide information regarding particular embodiments and examples. These examples are meant to be illustrative only and not limiting. In one example, zirconyl nitrate solution [$Zr(NO_3)_4$] and Zinc nitrate [$Zr(NO_3)_4$] were dissolved in deionized (DI) water and heated to 75° C. The composition between the $Zr(NO_3)_4$ and $Zr(NO_3)_4$ varies based on the final catalyst composition. The pH of the solution is initially about 1; potassium hydroxide is subsequently added to the solution until the pH of the solution reaches 10.5. This solution was stirred continuously and aged for approximately 22 hours at 75° C. The aged material was filtered and washed with deionized (DI) water at 85° C. until the dissolved solids in the wash solution reaches approximately 50 ppm. The washed material was dried overnight at 90° C., before the dried material is crushed to a fine powder and pelletized at 15,000 lbs pressure and sieved between 35 and 100 mesh. The sieved material is then calcined at 450° C. for 3 hours in a furnace. This material is denoted as the base (ZrO2-ZnO) mixed oxide material. This base mixed oxide material was then impregnated with various metals such as palladium (between 0.05 wt % and 0.5 wt %), silver (0.5 wt %), copper (1 wt %), and platinum (0.1 wt %). The impregnated material was then dried for about 2 hours and calcined again at 450° C. for 3 hours.

Various catalyst testing experiments were conducted on a down flow gas-phase reactor arrangement. The catalyst of interest was placed in the middle of the reactor tube in the isothermal zone and heated using a tube furnace. Ethanol or other oxygenate feeds and carrier gas nitrogen ($N_2$) was fed from the top of the reactor. The liquid product samples were collected in the bottom of the reactor in a cold trap (ice bath) arrangement. The collected liquid products were analyzed by gas chromatography-flame ionization detector (GC-FID) and by gas chromatography/mass spectrometry (GC-MS). The non-condensable gases from the cold trap passed through the flow meter and were analyzed by gas chromatography-thermal conductivity detector (GC-TCD). The gas samples were collected on an interval of every 1 hour and the liquid samples were collected every 12-24 hours. The catalysts were tested at temperature between 200° C. and 400° C., pressure between atmospheric and 500 psig, and weight hourly space velocity between 0.1 $hr^{-1}$ and 1 $hr^{-1}$. Various results of catalytic testing obtained under these conditions for ethanol conversion are summarized in FIGS. 3 (a)-(g) as prior art.

Developing technologies that fit the (ethanol) biorefinery concept to generate fuels and chemicals in tandem via simple and economical pathways that have flexibility based on the market demand is highly valuable. One of the major advantages of using ethanol as a bioproduct intermediate is that it can be derived from a wide variety of feed sources such as cellulosic biomass, algae, wet waste, coal, biogas and flue gas. The ketone-based pathway to transform ethanol into fuels and co-products will be complimentary to current ethanol conversion pathways and beneficial towards realizing the biorefinery concept through the development of new renewable technologies, enabling the production of fuels and high value co-products such as oxo-alcohols, plasticizer alcohols, detergent alcohols, lubricants, food aroma and fragrant agents that are otherwise produced from fossil fuel-derived resources.

Higher alcohols such as 1-butanol can be generated from both biochemical (Acetone-Butanol-Ethanol fermentation) and thermochemical (Guerbet ethanol coupling) processes. Catalysts that can work with alcohols irrespective of the carbon number to generate higher ketones will be beneficial for the alternative chemical and fuel industry and provides feedstock flexibility. The $ZrO_2$—ZnO catalyst is very flexible in converting ethanol, higher carbon number alcohols such as 1-butanol, and mixture of oxygenates (Acetone-Butanol-Ethanol) to higher ketones very selectively. This is significant as higher ketones generated from alcohols can be converted to infrastructure compatible transportation fuels (e.g. jet fuel, diesel) and commodity chemicals (e.g. plasticizer alcohols, lubricant alcohols).

Figure 4:
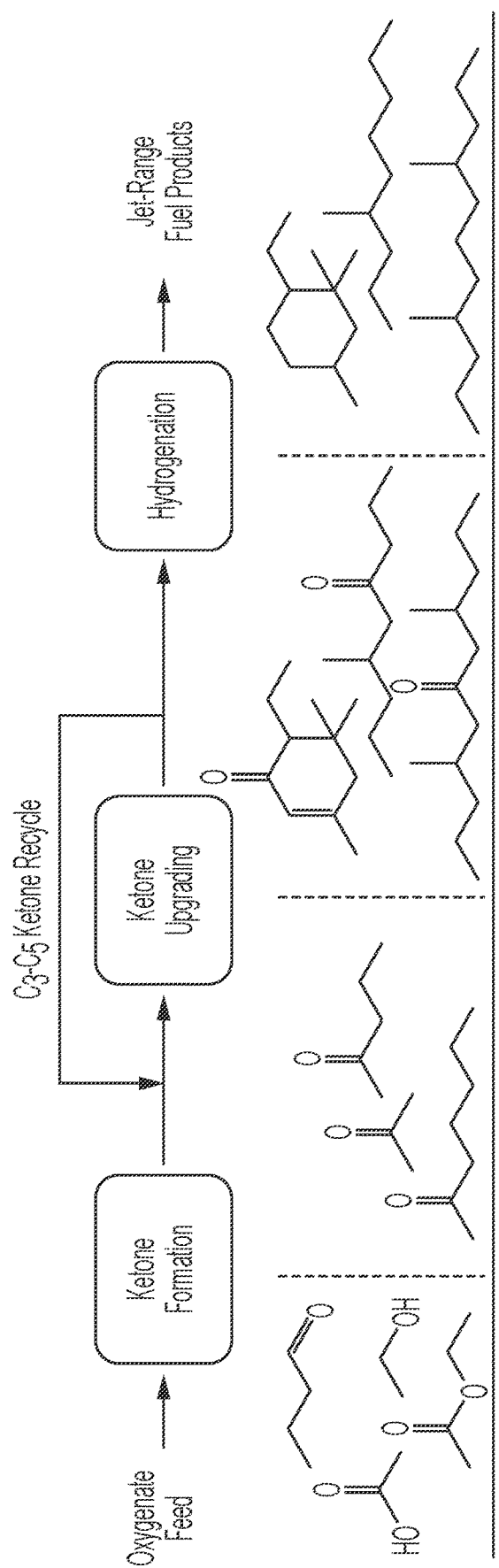
FIG. 4 shows the process flow diagram for the proposed ethanol to (jet) fuel process.

FIG. 4 shows the process flow diagram of the ethanol to (jet) fuel processes via ethanol to $C_{5+}$ ketones process. This process configuration provides a variety of advantages over other ethanol to (jet) fuel technologies. Various potential high value co-product insertion points at different stages of the process exist in the proposed process, including $C_{5+}$ ketones as fragrant and aroma agent and $C_{5+}$ alcohols as plasticizer/oxo-alcohols. $C_{5+}$ ketones are also intermediate feedstock to produce detergent alcohols and other co-products, providing potential flexibility between co-products and fuels based on the market needs. Generating co-product compounds from ethanol that retain the oxygen moiety significantly improves the overall product mass yield from the starting biomass. All major reactions achieve high conversion in a single pass (i.e. no recycle required), which may significantly reduce the capital and operational costs. Finally, hydrogen generated during the cross-aldol reaction is used in the downstream finishing step to produce long chain alcohol or fully saturated hydrocarbon fuels such as alkanes, isoalkanes, cyclo alkanes (required for jet fuel). This eliminates the process dependency on externally produced or purchased hydrogen, in stark contrast to most alcohol conversion processes.

The utilization of sustainable aviation fuels has been identified as one of the major mitigation strategies to address aviation's climate impacts. Among various renewable pathways, ethanol-to-jet (ETJ) offers an effective solution to produce large volumes of renewable jet fuel. However, the existing ETJ processes are not suitable for feed stocks with minor oxygenate impurities, necessitating the generation of a pure alcohol stream as feedstock. Due to a high degree of heterogeneity in renewable feedstocks (e.g. MSW), mixed oxygenate streams can be produced far more economically than pure ethanol streams. This creates the need to develop feed stock flexible technologies which can convert mixed oxygenates to sustainable aviation fuel.

This described process presents a selective pathway to produce jet-fuel from range of renewable feedstocks derived from waste streams or other sustainable sources. Small oxygenate compounds (e.g. alcohol, aldehyde, ester, ketone and carboxylic acids) can be effectively transformed into longer chain ketones through a condensation reaction at high selectivities and conversion over a Pd-promoted ZnO—

ZrO$_2$ catalyst. This ketone mix can be upgraded to jet-range oxygenate compounds through a number of reaction chemistries, such as cyclization to produce branched cyclohexenones ranging from C$_9$ to C$_{15}$, with the specific composition being controlled by changes in the feed composition and reaction conditions. Effective hydrodeoxygenation and hydrogenation yields a jet-fuel range product of branched alkanes appropriate for direct usage as fuel or blending as drop-in products.

Prior art demonstrated the development of a selective process to produce long chain oxygenates from a number of the from ethanol via the formation of a range of ketones, including acetone, 2-pentanone, and 2-heptanone from ethanol over a number of promoted mixed oxide catalysts, with Pd—ZnO—ZrO$_2$ exhibiting the highest performance due to the in-situ formation of a Pd—Zn alloy that promotes rapid dehydrogenation and hydrogen transfer while minimizing side product formation. It was previously shown that this process has a high selectivity to ketone products (>70%) with complete conversion of feed ethanol, as well as stable catalyst performance for lifetimes over 2000 hours time on stream. This process has several advantages beyond its high yield to ketones, the first being that it is also capable of accepting a wide range of mixed feeds beyond ethanol consisting of oxygenates with different functional groups and carbon lengths, including alcohols, aldehydes, esters, and carboxylic acids. This data is presented below in Tables 1-5 and compared at the same reaction conditions performed in a flow reactor at 370° C., 300 psig N$_2$, and 0.15 hr$^{-1}$ WHSV. Selectivities to ketones for each of these different feeds can be increased by tailoring the operating parameters for each of the specific feeds. This provides a significant advantage by granting wide coverage and applicability for many of the currently developed renewable feedstock sources and processes beyond ethanol. The fact that the reaction is relatively agnostic towards feed composition and produces a consistent profile of the C$_{2n-1}$ ketones also provides greater ease in the processing of mixed feed streams from different sources as well as recycle streams.

To demonstrate this, additional implementations of this process with other oxygenates has also been performed beyond the initial application of this catalytic approach with ethanol as described in prior art. Tables 1 and 2 show the conversion and conversion obtained by using various feedstock compounds over a 0.1% Pd—ZnO—ZrO$_2$ catalyst under the following conditions: alcohol/ester conversion at 370° C., pressure at 300 psig over a 0.1% Pd—ZnO—ZrO$_2$ catalyst. The Pd—ZrO$_2$—ZnO catalytic system converts 1-propanol primarily to 3-pentanone, 1-butanol primarily to 4-heptanone and 1-pentanol primarily to 5-nonanone primarily. Unlike ethanol, higher alcohols will likely not require condensation after cross aldol reaction, as the ketones produced are already in fuel range. Testing of C$_4$-C$_8$ esters similarly yielded high ketone formation through the ester dimerization and decomposition of the B-ketoester. (Table 3).

TABLE 1

Selectivity and Conversion of Alcohols over Pd—ZnO—ZrO$_2$ at 370° C., 300 psig, and 0.14 hr$^{-1}$ WHSV

| Compound | Conversion (%) | Selectivity (%) | | | | | | |
| --- | --- | --- | --- | --- | --- | --- | --- | --- |
| | | Alcohols | Aldehydes | Ketones | Esters | Cyclics | Alkanes | Alkenes |
| Ethanol | 99.52 | 1.38 | 0.32 | 71.23 | 0 | 0.74 | 5.09 | 6.56 |
| 1-propanol | 99.94 | 8.26 | 10.01 | 56.23 | 7.23 | 0.24 | 0.61 | 2.03 |
| 1-butanol | 99.85 | 2.91 | 17.62 | 57.00 | 4.14 | 0.19 | 1.65 | 3.78 |
| 1-pentanol | 99.75 | 1.03 | 1.05 | 83.52 | 0.05 | 2.20 | 3.60 | 3.21 |
| 2-pentanol | 99.76 | 2.76 | 0.46 | 60.13 | 0.00 | 0.74 | 1.17 | 29.71 |

TABLE 2

Ketone Selectivity of cross condensation of alcohols over Pd—ZnO—ZrO$_2$ at 370° C., 300 psig, and 0.14 hr$^{-1}$ WHSV

| Compound | Ketones Selectivity (%) | | | | | |
| --- | --- | --- | --- | --- | --- | --- |
| | Acetone | Pentanone | Heptanone | Nonanone | Undecanone | Tridecanone |
| Ethanol | 5.82 | 23.38 | 18.81 | 8.66 | 7.20 | 3.64 |
| 1-propanol | 0.25 | 52.47 | 2.00 | 0.43 | 0.00 | 0.08 |
| 1-butanol | 0.00 | 1.18 | 54.16 | 1.50 | 0.00 | 0.00 |
| 1-pentanol | 0.00 | 0.78 | 1.67 | 68.01 | 5.49 | 7.14 |
| 2-pentanol | 4.69 | 34.47 | 10.29 | 2.46 | 6.88 | 0.57 |

Mixtures of the oxygenates were found be similarly successful in the formation of the higher ketone products. Combinations of acetone, 1-butanol, and ethanol were tested over the Pd—ZnO—ZrO$_2$ catalytic system, and were found to produce primarily C$_7$ ketone products, along with minor fractions of C$_9$ and C$_5$ ketones similar to those found in ethanol condensation. Starting with mixed oxygenated feeds results in higher average carbon numbers were while still maintaining significant ketone diversity compared to single ketone compounds observed in single higher alcohols condensation experiments. Significant cross condensation between ketone and alcohol compounds as well as self-condensation ketone formation was observed. Additional cross condensation experiments replacing 1-butanol with butanal and butanoic acid resulted in

TABLE 3

Selectivity and Conversion of Esters and Aldehydes over Pd—ZnO—ZrO$_2$ at 370° C., 300 psig, and 0.14 hr$^{-1}$ WHSV

| Compound | Conversion (%) | Selectivity (%) | | | | | | |
|---|---|---|---|---|---|---|---|---|
| | | Alcohols | Aldehydes | Ketones | Esters | Cyclics | Alkanes | Alkenes |
| Ethyl Acetate | 100 | 0.76 | 0.90 | 42.88 | 0.00 | 3.39 | 0.53 | 23.82 |
| Ethyl Butyrate | 100 | 0.72 | 3.20 | 78.42 | 0.00 | 0.16 | 3.93 | 3.47 |
| Butyl Butyrate | 99.85 | 2.19 | 16.99 | 60.98 | 0.73 | 0.19 | 2.33 | 16.78 |
| Hexyl Acetate | 99.75 | 1.11 | 1.31 | 95.26 | 1.09 | 0.00 | 1.17 | 0.00 |
| Butanal | 99.76 | 2.76 | 0.46 | 60.13 | 0.00 | 0.74 | 1.17 | 29.71 |

TABLE 4

Selectivity and Conversion of Mixed Oxygenate Feeds over Pd—ZnO—ZrO$_2$ at 370° C., 300 psig, and 0.14 hr$^{-1}$ WHSV

| Compound | Conversion (%) | Selectivity (%) | | | | | | |
|---|---|---|---|---|---|---|---|---|
| | | Alcohols | Aldehydes | Ketones | Esters | Cyclics | Alkanes | Alkenes |
| Acetone-Butanol-Ethanol (3:6:1) | 99.52 | 3.65 | 6.54 | 76.19 | 1.12 | 0.74 | 0.36 | 4.48 |
| Butanol-Ethanol (2:1) | 99.85 | 2.01 | 9.63 | 66.66 | 0.22 | 0.19 | 1.39 | 10.39 |
| Acetone-Butanol (1:2) | 96.31 | 0.2 | 0.22 | 65.40 | 0.00 | 0.0 | 2.76 | 19.45 |
| Acetone-Butanal (1:3) | 95.16 | 5.27 | 2.67 | 69.08 | 0.00 | 0.81 | 6.03 | 7.03 |
| Acetone-Butyric Acid (1:3) | 94.75 | 0.78 | 2.10 | 72.22 | 1.81 | 0.92 | 3.42 | 7.99 | similar product profiles with predominantly $C_7$ products, demonstrating that this catalytic approach is equally effective in transforming oxygenates with differing functional groups.

Potential feedstocks may often have significant water content such as from fermentation processes or catalytic approaches based on aldol condensation through subsequent elimination of water. Catalytic performance of the Pd—ZnO—$ZrO_2$ system under previously described reaction conditions performed similarly resulting in high ketone selectivities when fed Ethanol and ABE streams with significant water content (50 wt %), as shown in Table 5. Optimal yields to 2-pentanonea and acetone were observed at 340° C. for ethanol and 370° C. for acetone-butanol-ethanol mixtures. Increased water in the reaction improves the overall ketone formation rate by promoting the ketonization pathway over condensation. High tolerance for water significantly broadens the potential feed sources for this process and reduces operational costs by eliminating otherwise necessary prior steps such as azeotropic separation.

acid catalysts such as zeolites, resulting in aromatic fuel compounds that are generated in typical petrochemical processes in the production of conventional jet fuel.

Trimerization via condensation chemistry or cyclization, via condensation followed by Michaels addition, of smaller ketones presents an alternative, potentially superior approach to aromatization. As these reactions have the potential to produce both branched ketones as well as cyclic ketones which may be hydrogenated to branched alkanes and cycloalkanes respectively. It is desirable for synthetic jet fuels to contain some fraction of aromatic hydrocarbons, as many elastomer seals rely on swelling caused by aromatic compounds to seal well. However, large aromatic fractions also cause increased soot formation during combustion; thus, a mixture of aromatics and linear or branched alkanes is often desired. Aromatics could potentially be replaced by cycloalkanes, since the preliminary studies on these compounds have shown promising seal swelling properties.

TABLE 5

Selectivity and Conversion of wet oxygenate feeds over Pd—ZnO—$ZrO_2$ at 370° C., 300 psig, and 0.14 $hr^{-1}$ WHSV

| Feed | Temperature (° C.) | Conversion (%) | Selectivity (%) | | | | | |
|---|---|---|---|---|---|---|---|---|
| | | | Alcohols | Aldehydes | Ketones | Esters | Cyclics | Alkanes | Alkenes |
| 50% $H_2O$ 50% Ethanol | 300 | 57.75 | 1.38 | 16.52 | 20.14 | 59.00 | 0.00 | 0.25 | 0.08 |
| | 340 | 92.99 | 3.74 | 3.00 | 72.37 | 1.65 | 0.00 | 0.48 | 0.86 |
| | 370 | 100.00 | 1.61 | 0.00 | 49.42 | 0.00 | 0.00 | 2.46 | 19.77 |
| 50% $H_2O$ 50% Acetone-Butanol-Ethanol (3:6:1) | 370 | 99.85 | 0.72 | 0.00 | 68.88 | 0.00 | 0.00 | 0.47 | 11.49 |

Figure 5:
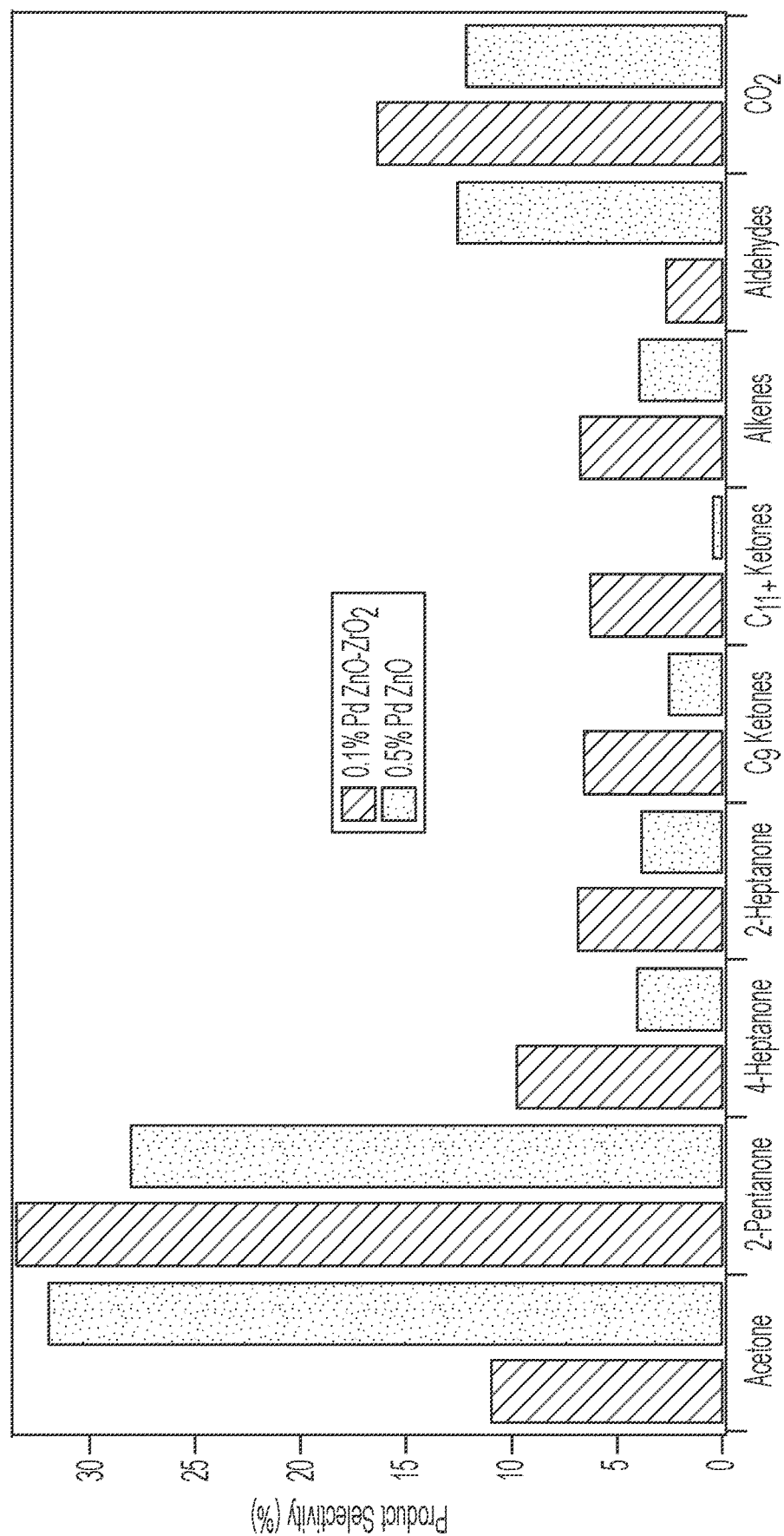
FIG. 5 shows the results testing the ethanol cross aldol condensation reaction over two dissimilar catalysts.
Figure 6:
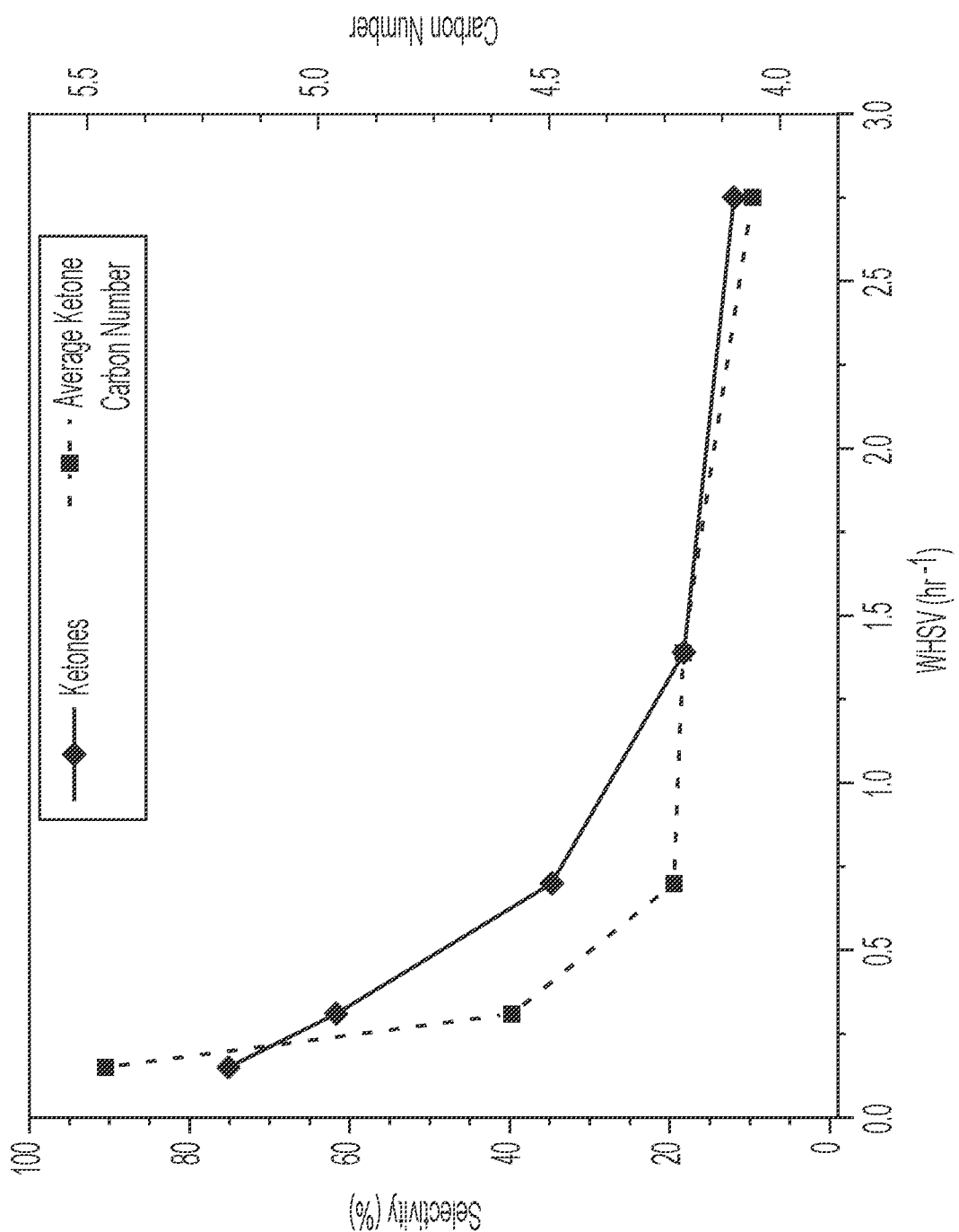
FIG. 6 shows the change in ketone selectivity and average carbon with weight hourly space velocity.
Figure 7:
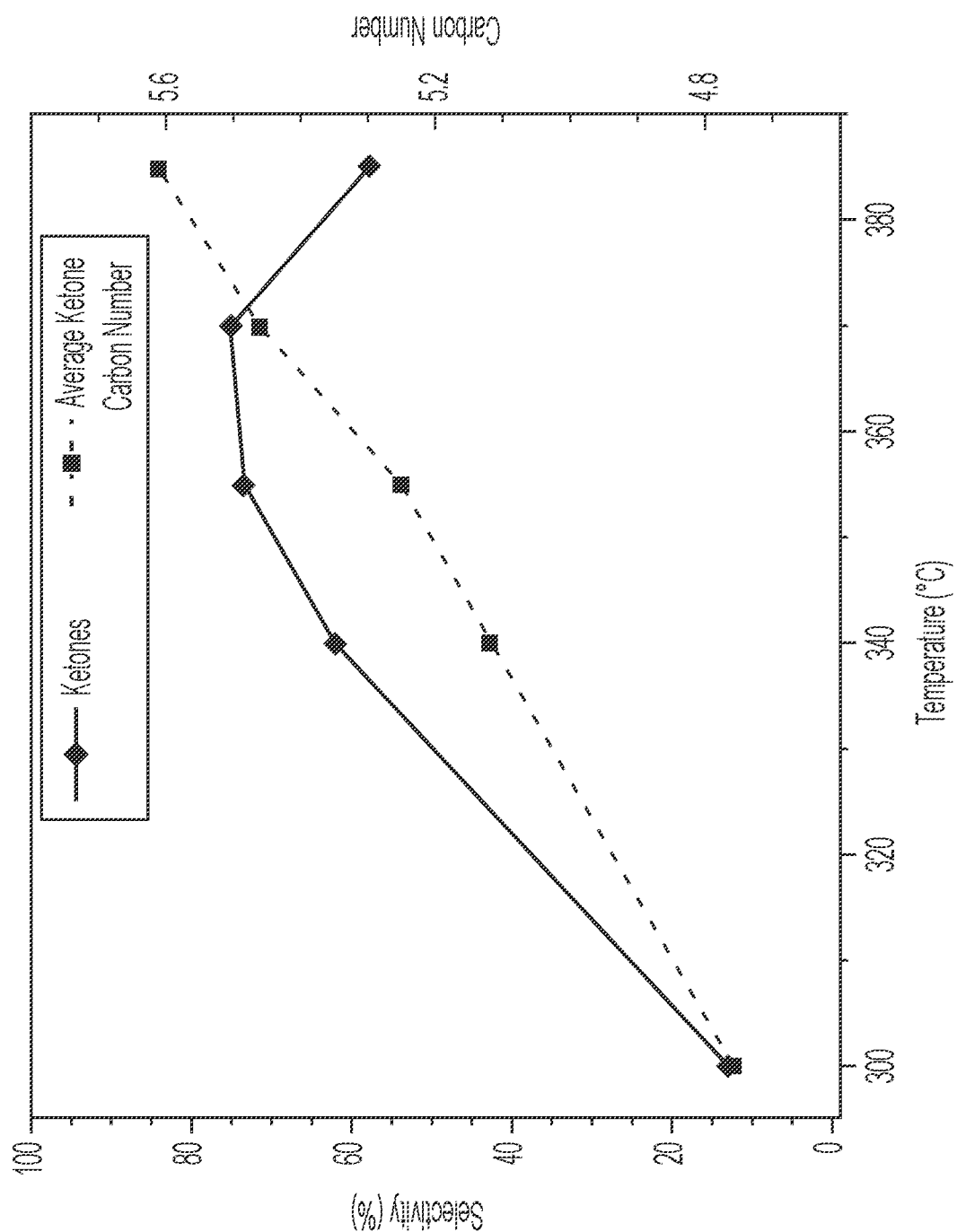
FIG. 7 shows the change in ketone selectivity and average carbon with temperature.

Another major advantage of the cross-aldol chemistry lies in the degree of control over the reaction product profile which significantly impacts the compounds ultimately produced at the end of the process. Altering the relative carbon number distribution of the produced ketones can be achieved through modification of the catalyst formulation. Two clear examples of different product profiles are shown in FIG. 5, with longer and shorter chain ketones being produced over 0.1% Pd—ZnO—$ZrO_2$ and 0.5% Pd—ZnO, respectively, at the same reaction conditions reported in previous experiments. Alterations to the acid and base characteristics of oxide support, which can be easily achieved through adjusting the ratio of Zn to Zr during catalyst synthesis, can also result in differences in the degree and location of branching in ketone products. Changes in the operating conditions can be used to achieve a similar effect; the average ketone carbon chain length can be varied from ~4 to ~6 by lowering the weight hourly space velocity from 0.69 to 0.15 $hr^{-1}$ or increasing the reaction temperature from 340° C. to 370° C., as shown in FIGS. 6 and 7. Facile control of these ketone products is critical to adjusting and optimizing the downstream processes to generate fuel products with desired properties and specifications.

Following the formation of the ketone mixture from the first step, the ketones with carbon numbers lower than typically expected for jet-range compounds must be further upgraded, for which several catalytic strategies can be implemented depending on the precise mixture of ketones generated in the initial ketone formation step. Most directly, longer ketone products ($C_5$+) can be dimerized through condensation chemistry to generate fuel range linear oxygenates ($C_{10+}$). Smaller ketones can be aromatized using the Cyclization of the smallest ketone product, acetone is known to selectively form isophorone, a 9-carbon unsaturated cyclic ketone. This cyclization strategy can be applied to other secondary ketones to produced other branched cyclohexenone products, typically performed via aldol condensation chemistry over basic oxide catalyst such as MgO—$Al_2O_3$ hydrotalcite type catalysts.

In one specific case a MgAl hydrotalcite catalyst was synthesized via the co-precipitation of metal salt pre cursors from a homogenous mixed and titrated solution. Mg$(NO_3)_2$.$6H_2O$ and Al$(NO_3)_3$.$6H_2O$ were dissolved in aqueous solution in the desired stoichiometric Mg:Al ratio and pumped into a 60° C. solution of $Na_2CO_3$.$10H_2O$ that was titrated by 1 M NaOH, using a pH controller to automatically maintain a pH of 11. To introduce the Pd promoter, Pd$(NO_3)_2$.$xH_2O$ can be added to the initial precursor solution to obtain a calculated Pd loading in weight percent of the final catalyst. Under steady titration and vigorous mixing, a precipitate suspension was formed that was then aged for 20 hours at 60° C. The precipitate was separated by filtration and washed with 60° C. deionized water until ion concentrations dropped below 50 ppm in the wash effluent. The formed catalyst was dried overnight at 100° C., then pelletized at 16000 psig prior to calcination in air at 600° C. for 2 hours with 4° C./min ramping, and subsequent sizing between 35-100 mesh sieves. This material can be denoted as the base MgO—$Al_2O_3$ catalyst or Pd—MgO—$Al_2O_3$. Pd promotion of the base MgO—$Al_2O_3$ can be also be achieved through other methods such as impregnation.

Experiments performed in which 2-pentanone is reacted over a MgO—$Al_2O_3$ catalyst produce almost entirely $C_{15}$ cyclics (e.g., 1-methyl-1-1,3-dicpropylcyclohexane) (FIG.

Figure 8:
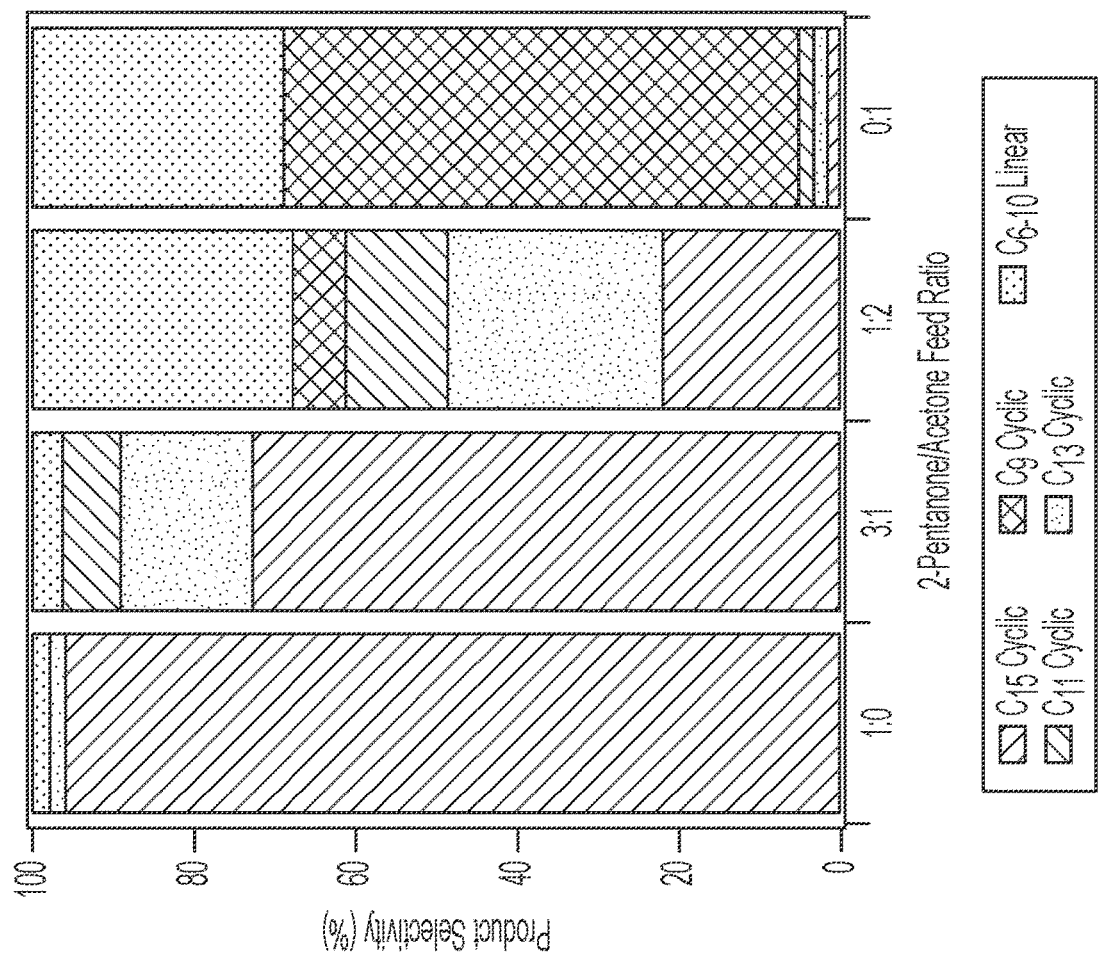
FIG. 8 shows the results of testing the cyclization of representative ketones during ketone upgrading.

8). However, cyclization of a mixed ketone feed yields a product profile with significant diversity. For example, starting with a mixture of 2-pentanone and acetone yielded a well distributed range of cyclic ketone products ranging from $C_9$-$C_{15}$ in size. Experimental results demonstrating this effect are presented in FIG. 8 showing the product selectivity for cyclic and dimer products with 2-pentanone to acetone feed ratios of 1:0 to 0:1 over a MgO—$Al_2O_3$ catalyst, at 200° C., 150 psig, and at a WHSV of 0.25 $hr^{-1}$. Stable performance was observed over the course of testing (up to 105 hours) in each case with conversion of acetone and 2-pentanone between 30 and 50%.

Figure 9A:
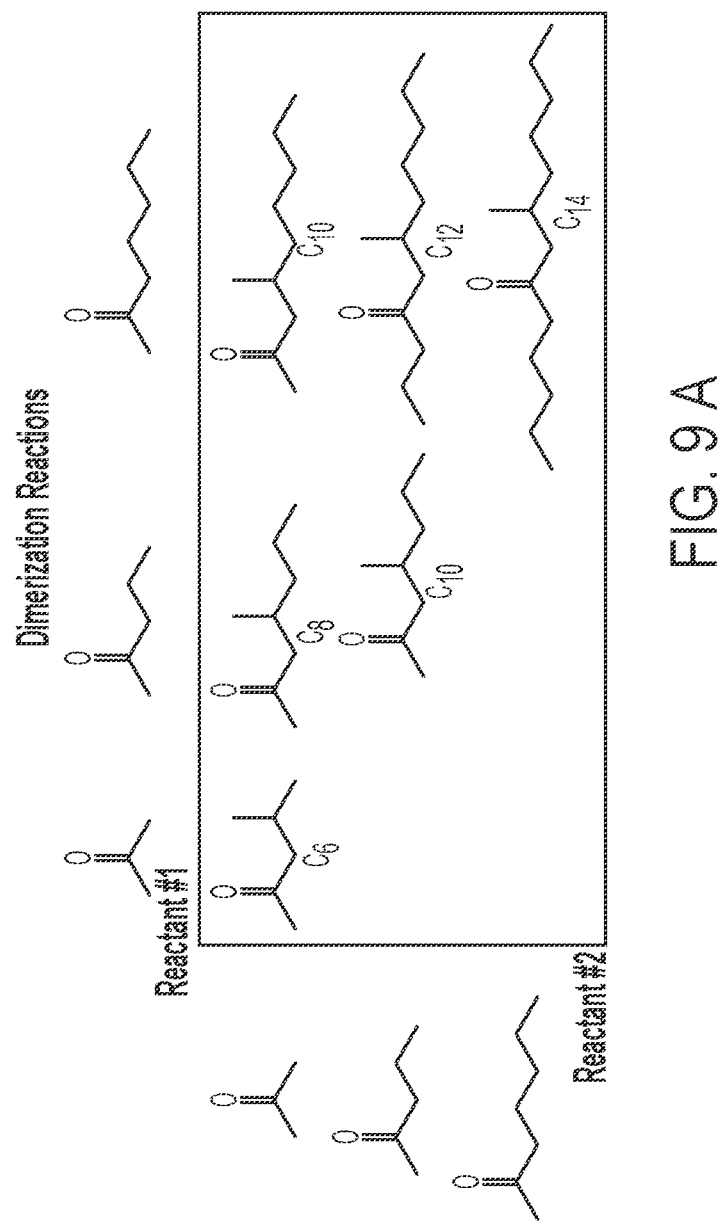
FIGS. 9A-9C show representative dimerized, trimerized, and cyclized ketone products obtained during ketone upgrading of representative small ketones.
Figure 9C:
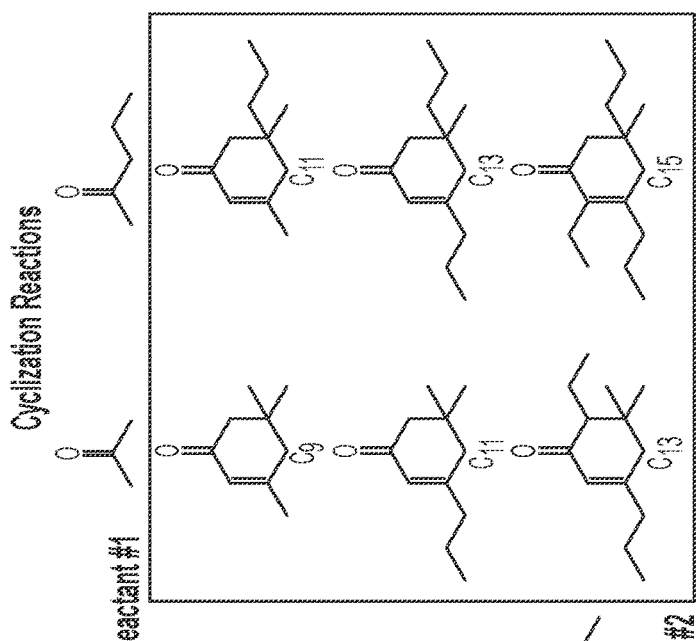
Figure 9B:
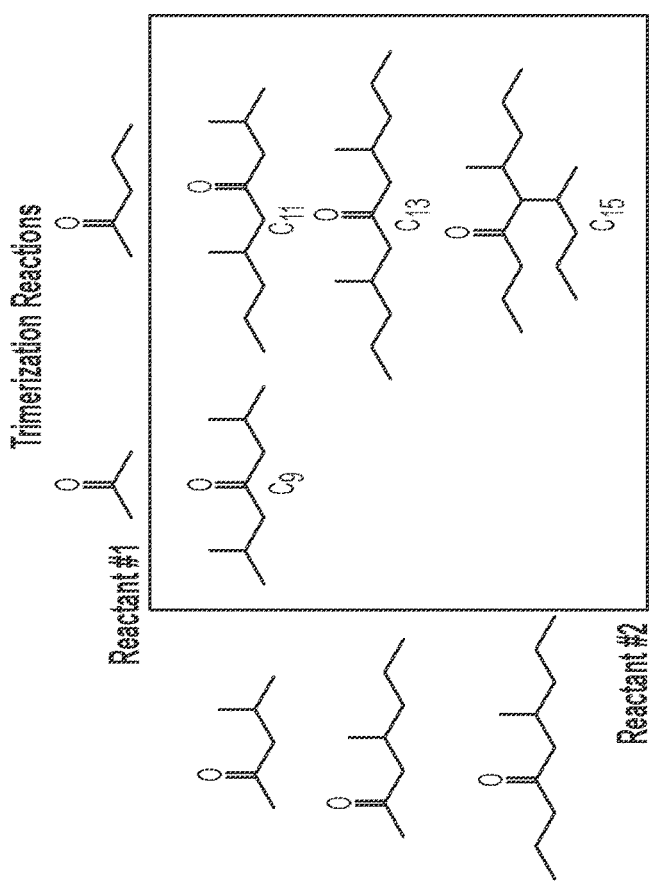
Figure 10:
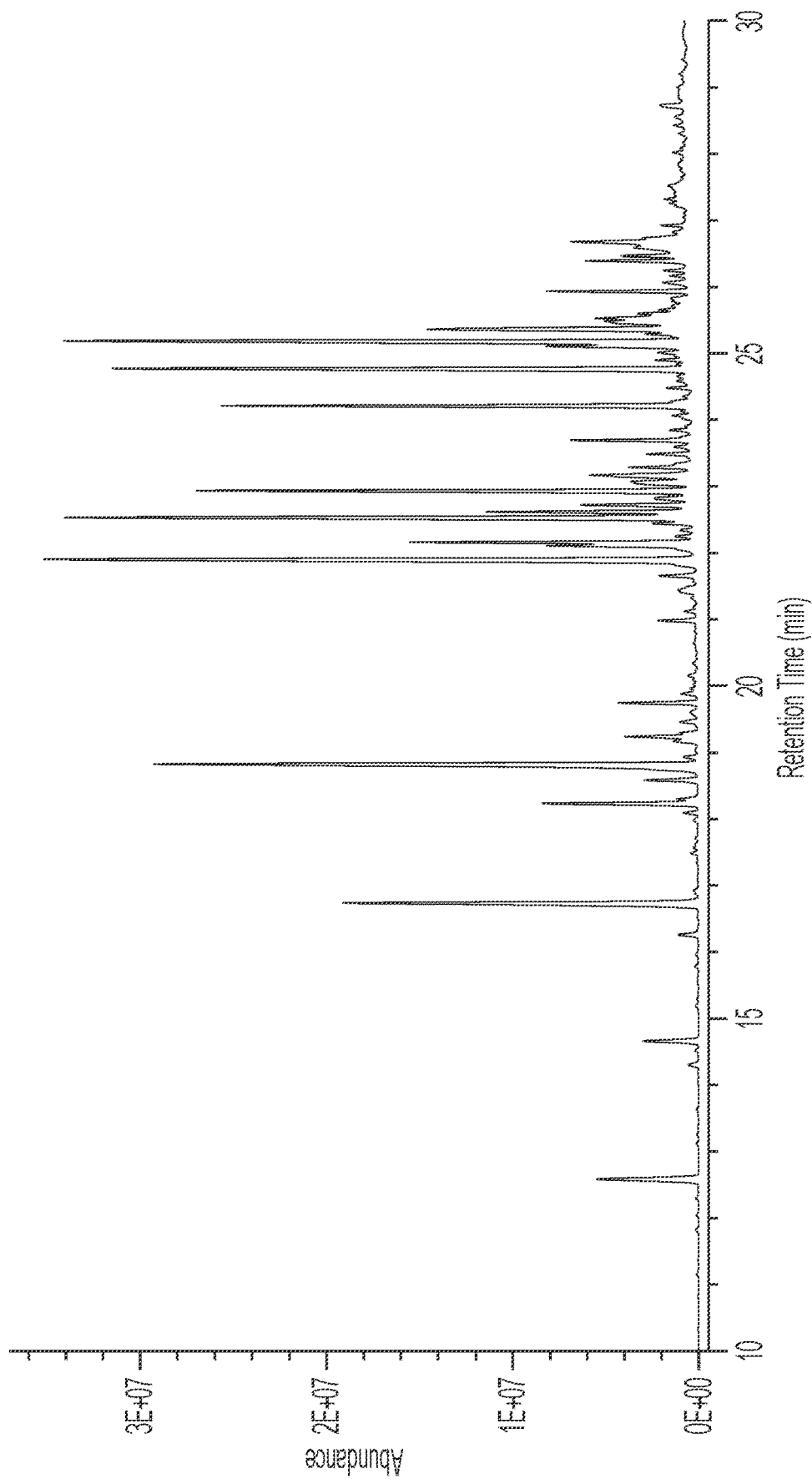
FIG. 10 shows the GC-MS chromatogram of hydrogenated cyclic alkanes product derived from ketone mixtures

Several research groups have demonstrated substantially higher conversions in the condensation of ketones by introducing catalytic sites capable of hydrogenation. Initial dimerization of ketones yields an unsaturated ketone which may participate in a Michaels addition reaction to form a cyclic ketone. However, if this unsaturated ketone is hydrogenated the Michaels addition reaction is not possible and additional condensation steps may occur forming branched trimers. By including small amounts of palladium on the MgO—$Al_2O_3$ catalyst and performing reactions under flowing $H_2$ complex mixtures of acetone, 2-pentanone, and 2-heptanone are converted to fuel range ketones ranging from $C_6$ to $C_{15}$ (Table 6). Each experiment is conducted over a 0.1% Pd MgO—$Al_2O_3$ at 250° C., 50 psig, and a WHSV of 0.14 $hr^{-1}$. Given the flexibility of the cross-aldol reaction product selectivity (FIGS. 2 and 5) and the ease with which all major ketone products are condensed to form dimers and trimers (Table 6) the final fuel composition can be controlled via careful control of process parameters. FIG. 9 shows the potential forms of these dimer and trimer products as well as the cyclic ketones formed during cyclization.

TABLE 6

Conversion of ketone (s) mixtures at varying compositions and yield of the dimer and trimer ketone product

| Feed wt % ($C_3$:$C_5$:$C_7$) | Conversion (%) | Dimer/Trimer Ketone Yield (%) | | | | | | | | | |
|---|---|---|---|---|---|---|---|---|---|---|---|
| | | $C_6$ | $C_8$ | $C_9$ | $C_{10}$ | $C_{11}$ | $C_{12}$ | $C_{13}$ | $C_{14}$ | $C_{15}$ | $C_{>15}$ |
| 0:100:0 | 92.01 | — | — | — | 53.22 | — | — | — | — | 27.76 | — |
| 30:70:0 | 89.34 | 0.73 | 14.93 | 0.69 | 36.24 | 9.53 | — | 12.93 | — | 5.16 | — |
| 0:70:30 | 81.97 | — | — | — | 35.43 | — | 18.29 | — | — | 1.87 | 4.98 |
| 25:50:25 | 92.30 | 0.70 | 8.53 | 0.84 | 22.77 | 10.14 | 2.92 | 12.79 | 6.70 | 10.29 | 3.87 |
| 40:40:20 | 90.26 | 2.99 | 14.76 | 6.96 | 13.19 | 15.90 | 4.35 | 7.40 | 5.33 | 8.16 | 0.71 |
| 20:40:40 | 90.07 | 1.36 | 7.33 | 1.09 | 16.38 | 3.14 | 16.53 | 5.78 | 8.04 | 7.86 | 7.97 |

Cycloalkanes are desirable in fuel blends for their energy density, improved fuel combustion (less soot formation) and seal swelling properties. However, fast hydrogenation of condensation products in dimerization/trimerization as shown above prevents the Michaels reaction which yields cyclic hydrocarbons. By utilizing ultra-low loadings of palladium in the MgO—$Al_2O_3$ catalyst it is possible to prepare catalysts that produce mixtures of dimers, cyclic trimers, and branched trimers from small ketones. Experiments conducted using a 2-pentanone feed over physical mixtures of a MgO—$Al_2O_3$ catalyst and a Pd MgO—$Al_2O_3$ catalyst, at 250° C., 50 psig, and varied WHSV (Table 7) under flowing hydrogen demonstrate that a mixture of these desired products can be formed given optimal conditions. This allows significant control over the final fuel mixture composition by altering a simple parameter (Pd loading) in the ketone upgrading reactor.

TABLE 7

Varying composition of 0.01% Pd/MgAl:MgAl on the 2-pentanone conversion to dimer, trimer and cyclic yield

| 0.01% Pd/MgAl: MgAl (wt %) | WHSV ($hr^{-1}$) | 2-Pentanone Conversion (%) | $C_{10}$ Yield (%) | Branched $C_{15}$ Yield (%) | Cyclic $C_{15}$ Yield (%) |
|---|---|---|---|---|---|
| 100:0 | 0.145 | 92.01 | 53.22 | 27.76 | 0.00 |
| 50:50 | 0.29 | 61.23 | 51.20 | 5.04 | 6.24 |
| 5:95 | 0.073 | 59.79 | 23.70 | 1.35 | 31.39 |
| 1.3:98.7 | 0.073 | 42.73 | 3.61 | 0.33 | 37.37 |
| 0:100 | 0.073 | 42.52 | 2.95 | 0.29 | 38.31 |

Following the formation of jet-range oxygenate compounds, a hydrodeoxygenation process that both removes the ketone functionality as well as hydrogenates the unsaturated compounds to form alkanes is required that is effective for $C_{9-15}$ unsaturated cyclic ketone products $C_{8-14}$ unsaturated linear ketones. This chemistry can be achieved based on catalysts typically developed for hydrogenation of petroleum-based processes. As mentioned previously, hydrogen for this reaction can be carried over from the ketone formation step. Initial tests were performed on the $C_{9-15}$ cyclic and linear ketone mixtures generated previously over MgO—$Al_2O_3$, using the nickel-based hydrogenation catalyst. All tested mixtures were successfully hydrogenated with >99% conversion over the catalyst.

The desired branched cycloalkanes and linear alkanes were the primary products, with only small traces of oxygenated intermediates and C—C cleavage products observed. To perform a comparable analysis for the final generated cycloalkane-rich mixture, the mixtures were distilled into three major cuts: 0-155° C., 155-260° C., and >260° C. The $C_9$ and $C_{15}$ mixtures resulted almost entirely in their respective alkane products, with mixed ketone (acetone/2-pentanone) feed being necessary to generate a well-distributed product profile with a combination of branched and cyclic linear products, as shown in the chromatogram from the GC-MS analysis presented in FIG. 8. The distribution of alkanes in the product composition was found to be 1.0% n-alkanes, 11.0% iso-alkanes, 78.0% monocycloalkanes, and 9.0% dicycloparaffins, with an average carbon number between 11 and 12.

Figure 11:
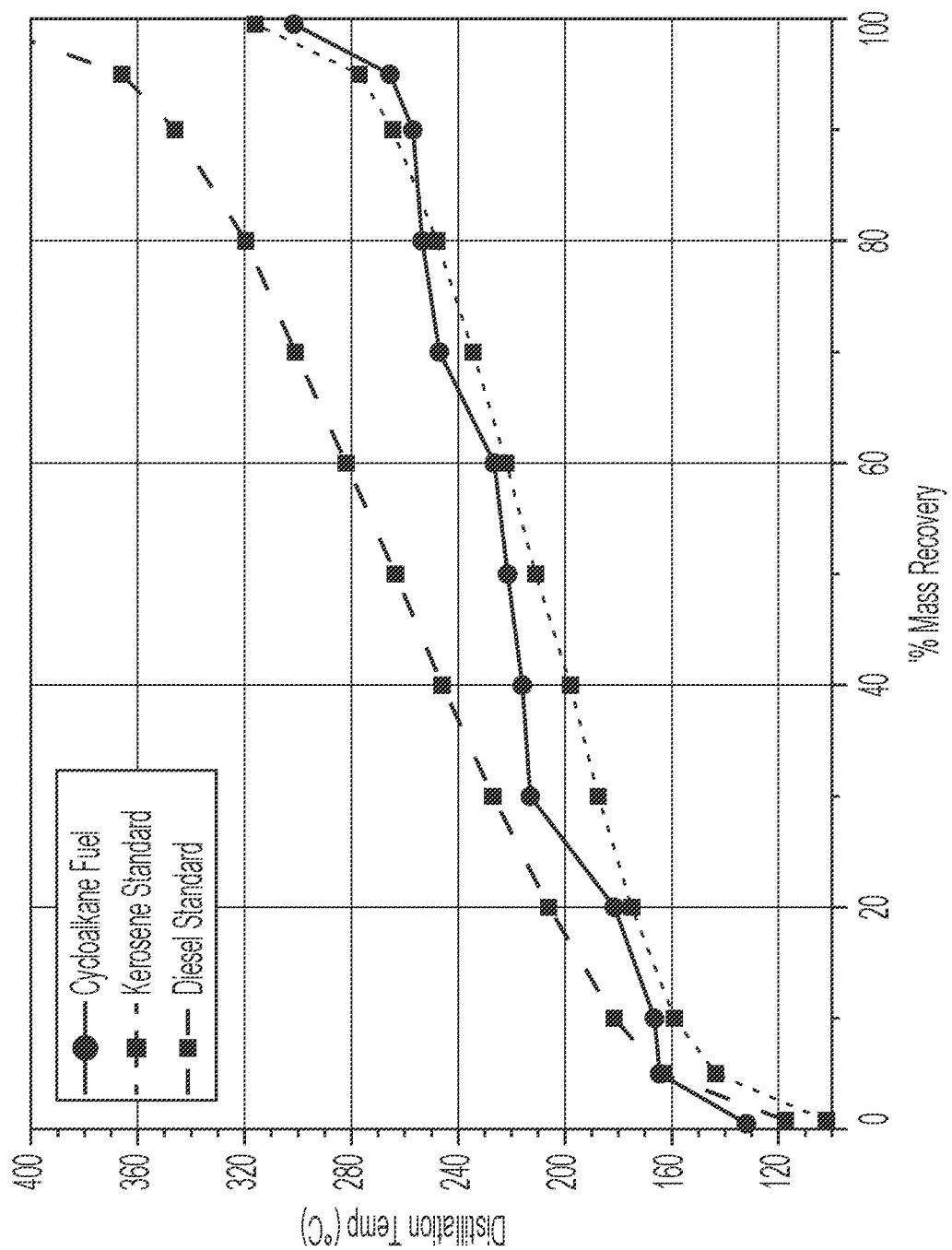
FIG. 11 shows the simulated distillation curve for ketone-derived $C_9$-$C_{15}$ cycloalkane fuel
Figure 12:
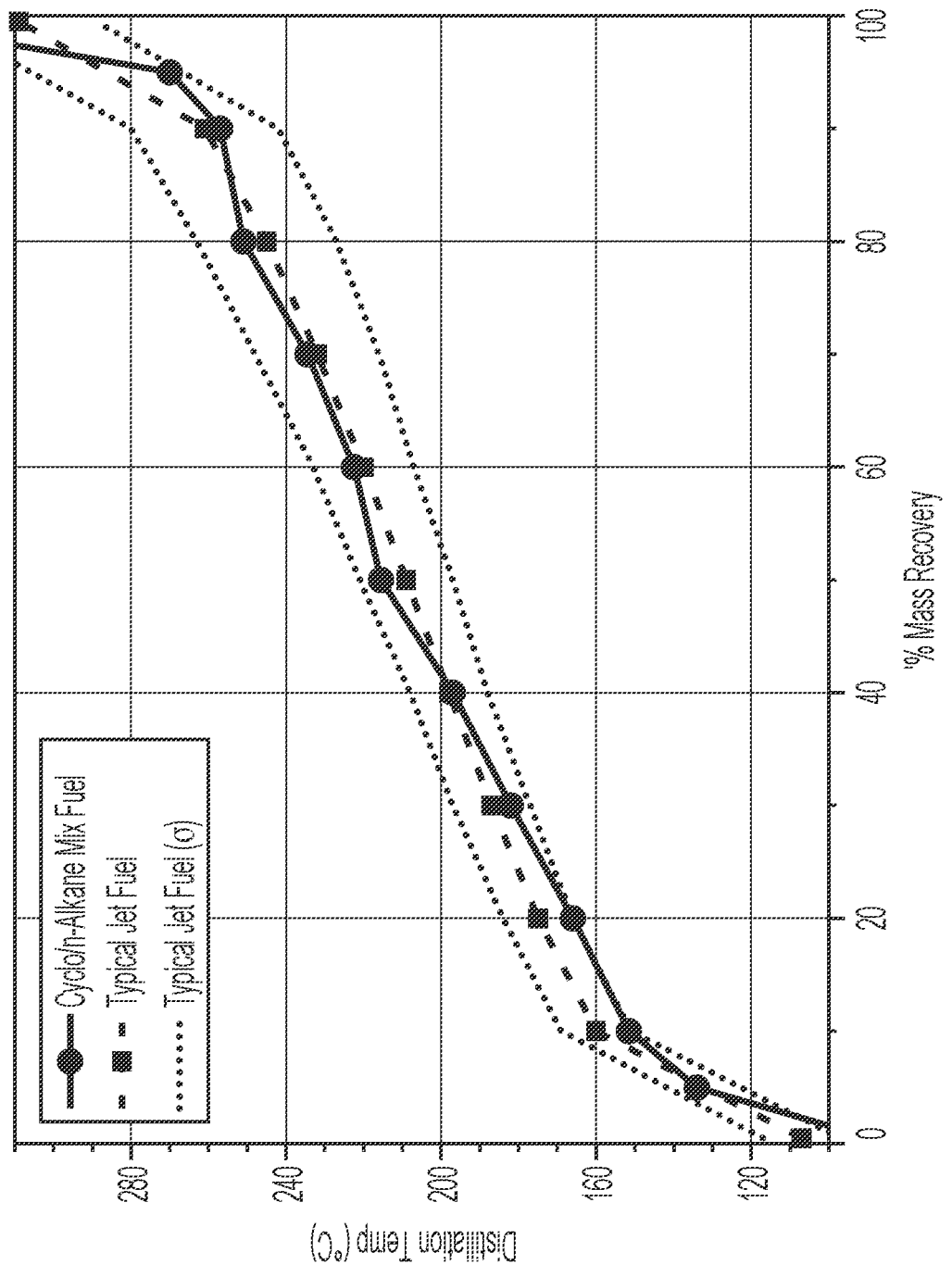
FIG. 12 shows the simulated distillation curve for ketone derived $C_9$-$C_{15}$ cyclic and branched alkane mixed fuel

The resulting boiling point distribution curve of the 155-260° C. distillate cut of hydrogenated cycloalkane fuel derived from $C_3$-$C_5$ ketone cyclization is compared with those of kerosene and diesel fuels, as shown in FIG. 11. As expected based on the product distribution, the $C_{9-15}$ mixture generated from mixed ketone cyclization resulted in a smoother, less stepped curve that adheres closely to the kerosene standard compared to the products of single ketone cyclization (e.g. isophorone). Further improvements to distillate fuel quality can be made by mixing in jet-range n-alkane and iso-alkanes compounds derived from the dimerization/trimerization and hydrotreating of higher ketones produced from mixed oxygenated feeds. The resulting product profile becomes more diversified which is reflected in the improved smoothness of its boiling point distribution curve, presented in FIG. 12. Results compare favorably to tested jet fuels with the entire curve falling well within one standard deviation of the typical boiling point distribution curves from measured jet fuels. Here the advantages of this overall ketone upgrading process starting from mixed oxygenate feeds are evident; the variation in carbon number and structures of the resultant end compounds yield a more consistent product with properties more likely to match that of conventional aviation fuel and more easily serve as a drop-in fuel source. Previously discussed Pd modification of the trimerization/cyclization catalyst to adjust cyclic to branched alkane ratios thus provide a direct way to improve the performance of the final aviation fuel.

While various preferred embodiments of the disclosure are shown and described, it is to be distinctly understood that this disclosure is not limited there to but may be variously embodied to practice within the scope of the following claims. From the foregoing description, it will be apparent that various changes may be made without departing from the spirit and scope of the disclosure as defined by the following claims.

What is claimed is:

1. A method for forming a desired hydrocarbon fuel product from a mixed oxygenate feed comprising the steps of:
   forming ketones from the mixed oxygenate feedstock by passing the mixed oxygenate feedstock over a preselected catalyst under preselected conditions;
   upgrading the ketones by reacting the ketones under preselected conditions;
   recycling selected upgraded ketones through the upgrading process to obtain a branched cyclohexenone product; and
   hydrogenating the branched cyclohexenone product to obtain the desired hydrocarbon fuel product.

2. The method of claim 1 wherein the mixed oxygenate feedstock includes alcohols, aldehydes, esters, and carboxylic acids.

3. The method of claim 1 wherein the ketones are $C_{2n-1}$ ketones.

4. The method of claim 1 wherein the forming of ketones includes passing the mixed oxygenate feedstock over a catalyst selected from the group consisting of 0.1% Pd—ZnO—$ZrO_2$ and 0.5% Pd—ZnO.

5. The method of claim 1 wherein the step of upgrading ketones includes passing the feedstock over a catalyst selected from the group consisting of 0.1% Pd—ZnO—$ZrO_2$ and 0.5% Pd—ZnO.

6. The method of claim 4 wherein the feedstock is passed at a weight hourly space velocity between 0.69 to 0.15 $hr^{-1}$.

7. The method of claim 4 wherein the reaction temperature at which the feedstock is passed over the catalyst is between 340° C. to 370° C.

8. The method of claim 1 wherein hydrogen gas generated in-situ through the formation of acetone is used in the hydrogenation step.

9. The method of claim 1 wherein the upgrading step includes dimerization over a catalyst selected from the group consisting of MgO—$Al_2O_3$ and 0.01% to 1% Pd—MgO—$Al_2O_3$.

10. The method of claim 9 wherein the dimerization is performed by condensation chemistry.

11. The method of claim 1 wherein the upgrading steps includes aromatization using an acid catalyst.

12. The method of claim 1 wherein the upgrading step includes trimerization of smaller ketones over a catalyst selected from the group consisting of MgO—$Al_2O_3$ and 0.01% to 1% Pd—MgO—$Al_2O_3$.

13. The method of claim 1 further comprising the step of performing a hydrodeoxygenation process to form alkanes, isoalkanes and cycloalkanes.

14. The method of claim 13 wherein the hydrodeoxygenation process includes passing $C_{9-15}$ cyclic and linear ketone mixtures over MgO—$Al_2O_3$, using a nickel-based hydrogenation catalyst.

* * * * *